(12) United States Patent
Wright et al.

(10) Patent No.: US 7,592,458 B2
(45) Date of Patent: Sep. 22, 2009

(54) DERMAL ANESTHETIC COMPOUNDS AND PHARMACEUTICAL COMPOSITIONS FOR INDUCING LOCAL ANESTHESIA AND MITIGATING NEUROPATHIC PAIN

(76) Inventors: George E. Wright, 298 Highland St., Worcester, MA (US) 01602; A. K. Gunnar Aberg, 902 Contento St., Sarasota, FL (US) 54242

( * ) Notice: Subject to any disclaimer, the term of this patent is extended or adjusted under 35 U.S.C. 154(b) by 0 days.

(21) Appl. No.: 11/880,270

(22) Filed: Jul. 20, 2007

(65) Prior Publication Data

US 2008/0033052 A1    Feb. 7, 2008

Related U.S. Application Data

(60) Provisional application No. 60/832,540, filed on Jul. 21, 2006.

(51) Int. Cl.
  *C07D 211/06* (2006.01)
  *A61K 31/445* (2006.01)

(52) U.S. Cl. .................. 546/205; 514/319
(58) Field of Classification Search ............. 546/205; 514/319
  See application file for complete search history.

(56) References Cited

U.S. PATENT DOCUMENTS

| | | | | |
|---|---|---|---|---|
| 3,923,813 | A | 12/1975 | Vanhoof et al. | 546/205 |
| 3,923,815 | A | 12/1975 | Vanhoof et al. | 260/293.62 |
| 3,923,887 | A | 12/1975 | Vanhoof et al. | 260/562 N |
| 3,943,172 | A | 3/1976 | Vanhoof et al. | 260/570.5 P |
| 4,822,597 | A | 4/1989 | Faust et al. | 424/48 |
| 4,942,175 | A | 7/1990 | Frawley, III | 514/535 |
| 5,000,950 | A | 3/1991 | Wuendisch | 424/78.06 |
| 5,227,165 | A | 7/1993 | Domb et al. | 424/450 |
| 5,234,957 | A | 8/1993 | Mantelle | 514/772.6 |
| 5,368,860 | A | 11/1994 | Sunami et al. | 424/448 |
| 5,446,070 | A | 8/1995 | Mantelle | 514/772.6 |
| 5,589,192 | A | 12/1996 | Okabe et al. | 424/486 |
| 5,667,799 | A | 9/1997 | Caldwell et al. | 424/449 |
| 5,776,952 | A | 7/1998 | Liedtke | 514/330 |
| 5,840,755 | A | 11/1998 | Liedtke | 514/535 |
| 5,863,941 | A | 1/1999 | Liedtke | 514/555 |
| 5,914,118 | A | 6/1999 | Yamamura et al. | 424/402 |
| 5,958,443 | A | 9/1999 | Viegas et al. | 424/427 |
| 5,968,536 | A | 10/1999 | Godfrey | 424/402 |
| 6,004,566 | A | 12/1999 | Friedman et al. | 424/400 |
| 6,031,007 | A | 2/2000 | Brodin et al. | 514/716 |
| 6,060,085 | A | 5/2000 | Osborne | 424/484 |
| 6,075,059 | A | 6/2000 | Reader | 514/738 |
| 6,103,771 | A | 8/2000 | Galer et al. | 514/456 |
| 6,113,921 | A | 9/2000 | Friedman et al. | 424/400 |
| 6,299,902 | B1 | 10/2001 | Jun et al. | 424/449 |
| 6,383,511 | B1 | 5/2002 | Cassel | 424/449 |
| 6,387,392 | B1 | 5/2002 | Saito et al. | 424/435 |
| 6,413,987 | B1 | 7/2002 | Aberg et al. | 514/319 |
| 6,455,544 | B1 | 9/2002 | Friedhoff et al. | 514/319 |
| 6,458,807 | B1 | 10/2002 | Pratt | 514/319 |
| 6,482,838 | B2 | 11/2002 | Pratt | 514/319 |
| 6,528,086 | B2 | 3/2003 | Zhang | 424/449 |
| 6,576,646 | B1 | 6/2003 | Pratt | 514/319 |
| 6,620,435 | B1 | 9/2003 | Osborne | 424/487 |
| 6,645,521 | B2 | 11/2003 | Cassel | 424/449 |
| 6,673,363 | B2 | 1/2004 | Luo et al. | 424/449 |
| 6,689,795 | B2 | 2/2004 | Pratt | 514/319 |
| 2001/0041166 | A1 | 11/2001 | Saito et al. | 424/49 |
| 2002/0022052 | A1 | 2/2002 | Dransfied et al. | 424/449 |
| 2003/0027833 | A1 | 2/2003 | Cleary et al. | 514/270 |
| 2003/0082225 | A1 | 5/2003 | Mason | 424/449 |
| 2003/0091619 | A1 | 5/2003 | Spencer | 424/449 |
| 2003/0124174 | A1 | 7/2003 | Galer | 424/449 |
| 2003/0138503 | A1 | 7/2003 | Staniforth et al. | 424/725.1 |
| 2003/0138505 | A1 | 7/2003 | Fischer et al. | 424/744 |
| 2003/0175328 | A1 | 9/2003 | Shefer et al. | 424/449 |
| 2004/0081681 | A1 | 4/2004 | Vromen | 424/449 |

FOREIGN PATENT DOCUMENTS

| | | |
|---|---|---|
| CA | 992547 | 7/1976 |
| CA | 997765 | 9/1976 |
| CA | 997786 | 9/1976 |
| CA | 1068289 | 12/1979 |
| EP | 0 321 870 | 12/1988 |
| EP | 0 742 207 | 11/1996 |
| EP | 1 216 685 | 6/2002 |
| GB | 1 321 424 | 6/1973 |
| GB | 1 405 444 | 9/1975 |
| GB | 1 468 347 | 3/1977 |
| WO | 91/07169 | 5/1991 |
| WO | 96/09829 | 4/1996 |
| WO | 96/33706 | 10/1996 |
| WO | 98/17263 | 4/1998 |
| WO | 00/76510 | 12/2000 |
| WO | 01/85139 | 11/2001 |
| WO | 04/000358 | 12/2003 |
| WO | 2004/047819 | 6/2004 |

OTHER PUBLICATIONS

T.W. Graham Solomons and C.B. Fryle Organic Chemistry, 9th Edition, John Wiley and Sons, Inc., pp. 183-184.*

(Continued)

*Primary Examiner*—Janet L Andres
*Assistant Examiner*—John Mabry
(74) *Attorney, Agent, or Firm*—Nields, Lemack & Frame, LLC

(57) ABSTRACT

The present invention relates to new tetralin compounds, the methods of preparing said tetralin compounds, the method of using said tetralin compounds as local anesthetics and dermal anesthetics, said compounds having particularly valuable properties as dermal and topical anesthetics in mammals, including man, as well as compositions containing said compounds.

14 Claims, 5 Drawing Sheets

OTHER PUBLICATIONS

Acta Pharmacol et toxicol, 1972, 31 p. 273-286; G.Aberg; "Toxicological and Local Anaesthetic Effects of Optically Active Isomers of Two Local Anaesthetic Compounds".

Dale et al. "Local anesthetic activity and toxicity of several esters of p-tert-butylbenzoic acid" CA 48:8416 (1953).

J.Org. Chem. 1996, 61, 3849-3861; Ahmed F. Abdel-Magid et al.; "Reductive Amination of aldehydes and Ketones with Sodium Triacetoxyborohydridge. Studies on Direct and Indirect Reductive Amination Procedures".

Vanhoof et al., caplus AN 1974: 403674.

International Search Report dated Jul. 25, 2008.

Vasoinhibitory Effects of NC 1005 and NC 1006, New Synthesized Antiarythmic Agents, In Isolated Rat Aorta, N. Stake, et al., Gen. Pharmac. vol. 25, No. 6, pp. 1149-1156.

Local Anesthetic Activity and Toxicity of Several Esters of p-Tertiary-Butylbenzoic Acid, Lamar B. Dale et al., Journal of the American Pharmaceutical Association, vol. XLII, No. 11, pp. 685-687.

Office Actions dated Nov. 5, 2008 and Jun. 4, 2008 in related U.S. Appl. No. 11/235,869.

Office Actions dated Oct. 24, 2008 and Jun. 3, 2008 in related U.S. Appl. No. 11/236,263.

* cited by examiner

¹HNMR spectrum of Example 3.

DERMAL ANESTHETIC COMPOUNDS AND PHARMACEUTICAL COMPOSITIONS FOR INDUCING LOCAL ANESTHESIA AND MITIGATING NEUROPATHIC PAIN

This application claims priority from provisional patent application Ser. No. 60/832,540, filed Jul. 21, 2006, the disclosure of which is hereby incorporated by reference.

TECHNICAL FIELD

This invention relates to new chemical entities of the General Formula 1 as shown below, compositions containing said chemical entities and to methods for the prevention and/or treatment of pain by administering said chemical entities and compositions. New chemical entities, comprising N-(1,2,3,4-tetrahydronaphth-2-yl)-N-phenyl-N-(alkylaminoalkyl) compounds of formula I, and the stereoisomers, the polymorphs and the pharmaceutically acceptable salts thereof are disclosed:

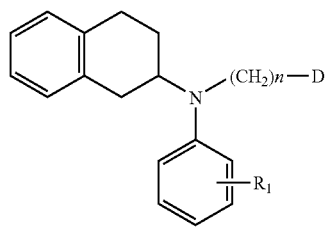

(Formula I)

wherein $R_1$ is, independently, one or more H, halo or lower (C1-C6) alkyl group(s), substituted at the 2, 3 and/or 4 positions of the phenyl ring, wherein n is 1, 2, 3 or 4 and wherein D represents a group of formula 2

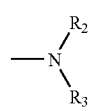

(Formula 2)

in which $R_2$ represents hydrogen, a lower alkyl or hydroxyalkyl radical containing 1 to 4 carbon atoms or a lower alkenyl or alkynyl radical containing 2, 3 or 4 carbon atoms, $R_3$ represents a lower alkyl or hydroxyalkyl radical containing 1 to 4 carbon atoms or a lower alkenyl or alkynyl radical containing 2, 3 or 4 carbon atoms, whereby $R_2$ and $R_3$ may be identical or different and may also form together with the adjacent nitrogen atom a nitrogenous heterocyclic ring, attached in any position and selected from the group consisting of un-substituted piperidino, pyrrolidino, pyridino, morpholino, quinuclidino, decahydroquinolino, decahydroisoquinolino and piperazino rings and substituted piperidino, pyrrolidino, morpholino, decahydroquinolino, decahydroisoquinolino and piperazino rings. When substituted, the nitrogen substituent of said rings is selected from the group consisting of methyl, ethyl, propyl, butyl, hydroxyethyl, hydroxypropyl or hydroxybutyl and where appropriate said nitrogenous heterocyclic ring is attached at the 1-, 2-, 3- or 4-position. Depending on the structures, there are two to four optical isomers. When there are four, the isomers are RR, SS, RS and SR and the racemic mixtures are RR/SS/RS/SR, RR/SS and RS/SR.

The chemical compounds of this invention have pharmacological properties that render said compounds useful in preventing and/or treating pain including neuropathic pain. The compounds can also be used to treat conditions, comprising convulsions, hiccup and cardiac arrhythmias and tinnitus.

Prevention and treatment of pain using the compounds of this invention may be achieved by applying the compounds or compositions containing said compounds on the skin or by applying the compounds or compositions containing said compounds on mucosal membranes of the body or by injecting said compounds or compositions containing said compounds to infiltrate biological tissues or by injecting said compounds or compositions containing said compounds in the anatomical proximity of nerves, thereby allowing said compounds to penetrate the biological tissues and cause analgesic activities, dermal anesthesia, topical anesthesia, infiltration anesthesia or nerve blocks.

The term "nerve block" as used herein encompasses local anesthesia of afferent or efferent nerves, and is also intended to include regional anesthesia, such as for example epidural anesthesia, spinal anesthesia, plexus blocks, and intravenous regional techniques. The term "infiltration anesthesia" as used herein refers to injection of a local anesthetic into the tissues to be anesthetized. The term "topical anesthesia" as used herein refers to the application of a composition containing a local anesthetic compound directly to mucous membranes of the body and to the anesthesia of body cavities, by injection, infusion or instillation of a composition containing at least one compound of the present invention into said body cavity, such as for example intrapleural anesthesia, intra-articular anesthesia and intravesical administration into the urinary bladder. The term "dermal anesthesia" refers to the anesthesia of the skin, the lips and other external tissues, usually by application of formulations containing a local anesthetic compound directly on the skin.

The terms "therapeutic amount" and "effective amount" as used herein are synonyms and refers to the amount of a compound of the present invention that offers therapeutic activity after administration to humans or animals. The therapeutic amount of local anesthetic compounds is usually referred to as concentration of the active compound in a composition and the volume administered of said composition. Thus, as an example 1 ml of a 1% solution equals an amount of 10 mg.

The invention also refers to compositions, containing at least one of said compounds of the Formula 1 and combinations of the present compounds with various other chemical entities such as for example penetration-promoting agents such as for example dimethylsulfoxide (DMSO). The duration of the local anesthetic activity may be prolonged by the use of vasoconstrictors such as for example epinephrine and may be interrupted or shortened by the use of vasodilators, such as for example phentolamine.

BACKGROUND OF THE INVENTION

Membrane stabilizing agents, such as lidocaine, prilocaine, mepivacaine and bupivacaine, have been shown to possess local anesthetic effects and are widely used for infiltration anesthesia and for inducing nerve blocks. These compounds have limited use as dermal anesthetics since they have to be given in high concentrations, which increase the risk of toxicity, tissue irritation and tissue damage. Other compounds, such as tetracaine, are better suited for dermal anesthesia since they may better penetrate through the tissues. However, tetracaine and similar drugs are known to cause tissue irritation and ester compounds, like tetracaine are unstable in the human body where practically all tissues contain esterases. Lidocaine also has analgesic activity and is applied dermally as a remedy for neuropathic pain (Lidoderm®).

Objectives of the present invention include providing compounds that are potent membrane stabilizing agents with a prolonged effect as when used to obtain infiltration anesthesia, nerve blocks, topical anesthesia and dermal anesthesia. anesthetics Further objectives of the present invention include providing said potent membrane stabilizing agents with beneficial penetration properties, making said compounds able to penetrate into the ocular tissues, the mucosal tissues, including rectal tissues, and also penetrate into human skin after application on the skin. Thus, the compounds of the invention have short onset time and long duration of anesthesia.

It is also an objective of the present invention to provide a method for analgesia, which is safe, effective, and has a minimum of side effects.

The mechanism of action of membrane stabilizing agents, when used to induce numbness, i.e., for infiltration anesthesia, nerve blocks, topical anesthesia and dermal anesthesia, is to inactivate ion channels in nerves and thereby inhibit neuronal impulse conduction. To do this, the membrane stabilizing compound needs to overcome the local penetration barriers and reach the nerve structure in a concentration that is high enough to achieve the therapeutic objective. The compounds of the present invention have the ability to effectively overcome such tissue penetration barriers.

The mechanism of the analgesic activity of compounds of the present invention, as well as lidocaine, in patients suffering from neuropathic pain, is not known, but is believed to be related to the known effects of these compounds on ion fluxes over biological membranes.

The term topical anesthesia is in this document defined as local anesthesia of mucosal membranes, such as for examples those of the eye, the ear, the mouth, the nose, the rectal area and the urogenital tract. The term dermal anesthesia is in this document defined as local anesthesia of the skin.

SUMMARY OF THE INVENTION

The present invention relates to new compounds and compositions as described above and to methods of inducing infiltration anesthesia, nerve blocks, topical and dermal anesthesia and to induce analgesia, by administering a composition containing at least one such compound that has good penetration properties and therefore can reach the site of action on the nerve ending or the nerve in a concentration that will block the initiation or conduction of nerve impulses. It has been found that compositions containing the compounds of the present invention are particularly useful for ocular and dermal anesthesia and for other forms of anesthesia, such as for example infiltration anesthesia and nerve blocks. The compounds of the invention are useful for local injections to paralyze small cutaneous smooth muscles that cause wrinkles of the skin, particularly facial skin in mature and older individuals. The compounds of the present invention are useful for the prevention of pain in connection with inserts of injection needle, surgical and dental procedures and for the treatment of pain in connection with the above mentioned medical procedures, insect bites, sunburn, hemorrhoids and for the treatment of neuropathic pain and urogenital pain. The compounds of the invention are also useful for individuals suffering from pruritus, such as for example pruritus caused by atopic dermatitis.

The present invention also provides effective methods for treating humans and animals, particularly-warm-blooded animals, with topical, dermal, infiltration and nerve block compositions, while reducing undesirable side effects, for example local burning and itching and particularly tissue toxicity resulting in necrosis.

DETAILED DESCRIPTION OF THE INVENTION

Figure 1:
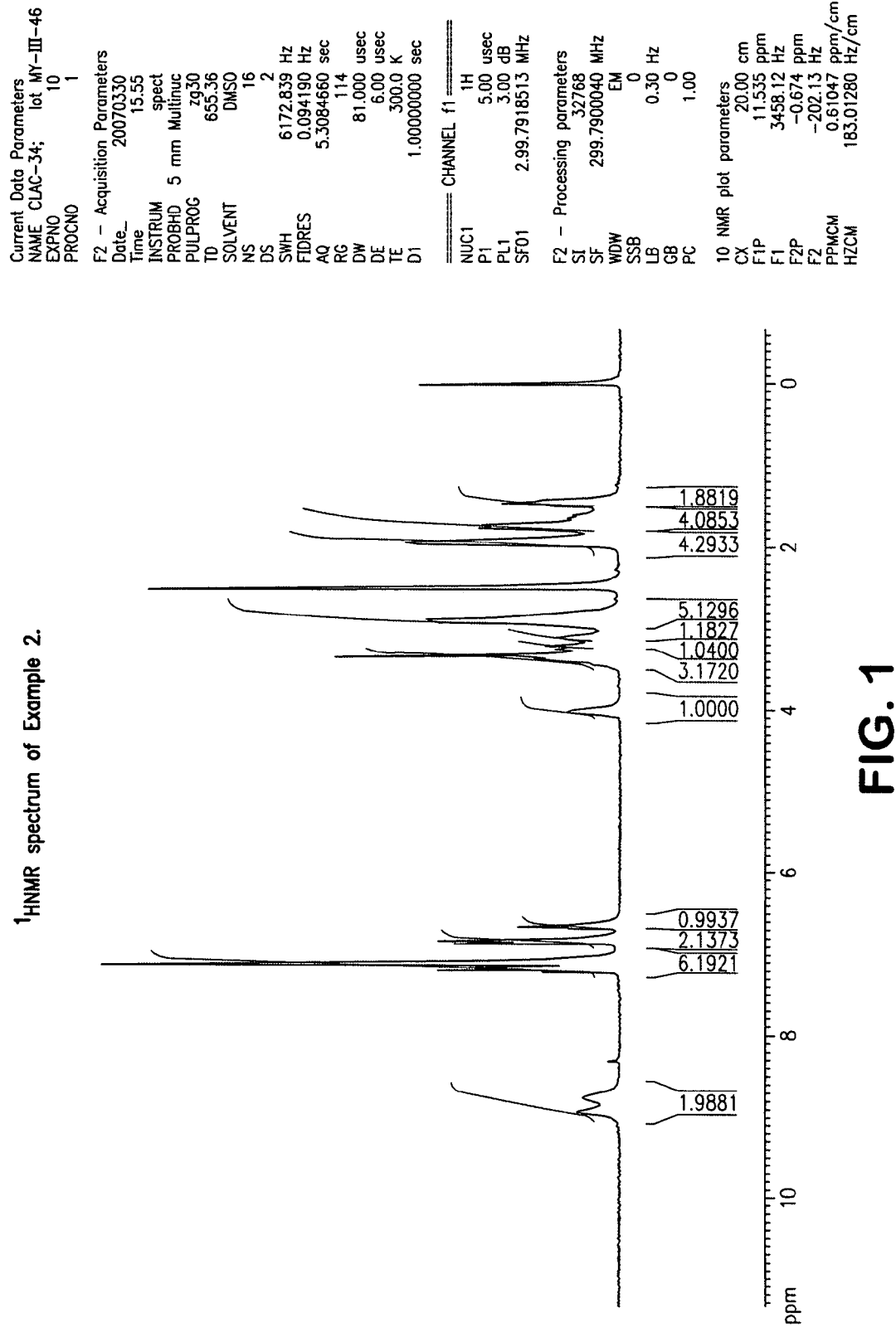
FIG. 1 is an NMR spectrum of the compound prepared in Example 2.

An objective of the present invention is to provide compounds that have analgesic activity as well as topical anesthetic, dermal anesthetic, infiltration anesthetic and nerve blocking activity and that can be administered either by injection or by topical or dermal application and that offer a short onset time and a long lasting effect.

It has now been found that compounds of the formulas below possess such properties.

Compounds of the invention are those of the general Formula 1:

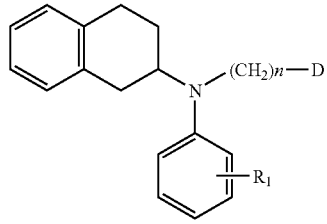

Formula 1 wherein $R_1$ is, independently, one or more H, halo or lower (C1-C6) alkyl group(s), substituted at the 2, 3 and/or 4 positions of the phenyl ring, wherein n is 1, 2, 3 or 4 and wherein D represents a group of formula 2:

Formula 2 in which $R_2$ represents hydrogen, a lower alkyl or hydroxyalkyl radical containing 1 to 4 carbon atoms or a lower alkenyl or alkynyl radical containing 2, 3 or 4 carbon atoms, $R_3$ represents a lower alkyl or hydroxyalkyl radical containing 1 to 4 carbon atoms or a lower alkenyl or alkynyl radical containing 2, 3 or 4 carbon atoms, whereby $R_2$ and $R_3$ may be identical or different and may also form together with the adjacent nitrogen atom a nitrogenous heterocyclic ring selected from the group consisting of unsubstituted piperidino, pyrrolidino, morpholino, piperazino, quinuclidino, decahydroquinolino, decahydroisoquinolino and pyridino rings and substituted piperidino, pyrrolidino, morpholino, piperazino, decahydroquinolino and decahydroisoquinolino rings. When substituted, the substituent of said ring is selected from the group consisting of hydrogen, methyl, ethyl, propyl, butyl, hydroxyethyl, hydroxypropyl or hydroxybutyl and where appropriate, said nitrogenous heterocyclic ring is attached to Formula 1 at the 1-, 2-, 3- or 4-position.

Preferred compounds of Formula 1 are those compounds where $R_1$ is hydrogen and n is 2. Particularly preferred compounds are the following compounds:

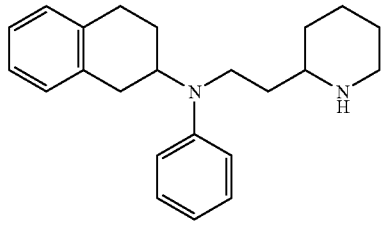

CLAC-34

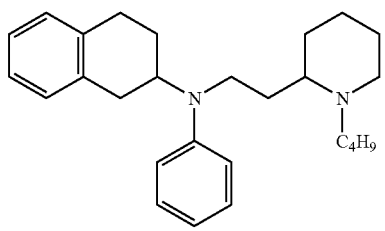

Bu-CLAC-34

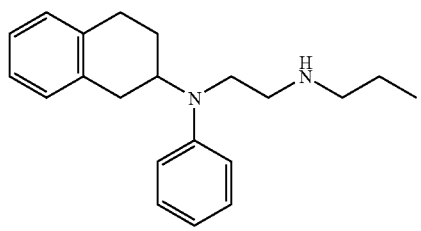

CLAC-HP

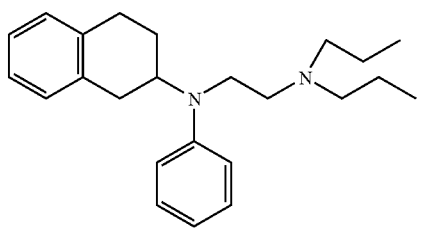

CLAC-PP

Depending on the process conditions and the starting materials, the end product is obtained either as the free base or as the acid addition salt, both of which are included within the scope of the invention. Thus, basic, neutral or mixed salts may be obtained, as well as hemi-, mono-, sesqui-, or polyhydrates. The acid addition salts of the compounds may be transformed in a manner known per se into free base using basic agents such as alkali or by ion exchange. On the other hand, the free bases obtained may form salts with organic or inorganic acids. In the preparation of acid addition salts preferably such acids are used which form suitable pharmaceutically acceptable salts. Such acids include hydrohalogen acids, sulfuric, phosphoric, nitric, and perchloric acids; aliphatic, alicyclic, aromatic, heterocyclic carboxy or sulfonic acids, such as acetic, formic, propionic, succinic, glycolic, lactic, malic, tartaric, citric, ascorbic, maleic, fumaric, hydroxymaleic, pyruvic, phenylacetic, benzoic, p-aminobenzoic, anthranilic, p-hydroxybenzoic, salicylic or p-aminosalicylic acid, embonic, methanesulfonic, ethane sulfonic, hydroxyethanesulphonic, ethylenesulphonic, halogenbenzenesulphonic, toluenesulfonic, naphtylsulfonic, or sulfanilic acids; methionine, tryptophane, lysine or arginine.

These and other salts of the new compounds, as e.g. picrates, may serve as purifying agents of the free bases obtained. Salts of the bases may be formed, separated from the solution, and then the free base can be recovered from the new salt solution in a purer state. Because of the relationship between the new compounds in free base form and their salts, it will be understood that the corresponding salts are included within the scope of the invention.

The starting materials are known or may, if they should be new, be obtained according to processes known per se.

The compounds of the present invention may be injected into the body of humans or animals as a solution or as a dry powder, using needle-free injector devices, such as for example Biojector 2000® by Bioject Medical Technologies, Inc. or Zingo® by Anesiva, Inc. Solutions containing the compounds of the present invention may of course be administered by injection or infusion, using suitable devices such as regular syringes or infusion devices, in the form of a pharmaceutical preparation which contains at least one compound of the invention either as a free base or as a pharmaceutically acceptable, non-toxic acid addition salt, such as for example hydrochloride, lactate, acetate, sulfamate, in combination with a pharmaceutically acceptable carrier. Usually the concentration of active compound in a solution for injection is between 0.01 and 10% by weight of the preparation. Preferred solutions for injection or infusion or infiltration may be prepared as aqueous solutions of a water soluble, pharmaceutically acceptable salt of the active compound, preferably in a concentration from 0.05 to 3.0% by weight. These solutions may also contain stabilizing agents, antibacterial agents, buffering agents and may be manufactured in different dosage unit ampoules, single-use syringes or bottles. In any case, the quantity of the formulation containing the drug to be administered will be determined on an individual basis, and will be based on the pharmacological potency of the drug, the route of administration and at least in part on consideration of the individual's size, the severity of the symptoms to be treated and the results sought. In general, quantities of a compound of the invention sufficient to eliminate the unwanted condition will be administered. The actual dosage (concentration and volume) and the number of administrations per day will depend on the pharmacokinetic properties of the drug and the mode of drug administrations, for example, for infiltration anesthesia of the skin. As an example, solutions containing 0.05% to 3.0% may be injected in doses varying from 0.1 ml to 10 ml may be used for injections, the actual concentrations and volumes depending on the tissue(s) being injected, the patient, the reason for inducing numbness and the effects sought.

The compounds and compositions also can be used in the treatment of tinnitus, such as by administering transdermally, such as with a patch, or intravenously (by injection or infusion).

In the present method, the compounds of the invention can be administered topically to ocular mucous membranes of the eye or the mucous membranes surrounding the eye. Formulations such as for example solutions, suspensions, gels or ointments may be useful. Compatible carriers, which may be used in this invention, comprise e.g. an aqueous solution, such as saline solutions, oil solutions or ointments. Formulations for ocular use may also contain compatible and pharmaceutically acceptable excipients, such as preservatives, surfactants, stabilizing agents, antibacterial agents, buffering agents and agents such as for example polymers to adjust viscosity, vasoconstrictors, antihistaminic agents or anti-inflammatory agents. These formulations may be manufactured in different dosage units, suitable for ocular administration. Also drug inserts, either soluble or insoluble, may be used. Usually the concentration of active compound in a formulation for ocular use is between 0.05 and 2.5% by weight. The quantity of the formulation containing the drug to be administered will be determined on an individual basis, and will be based on the pharmacological potency of the drug, the route of administration and at least in part in consideration of the individual's size, the severity of the symptoms to be treated and the results sought. In general, quantities of a local anesthetic compound of the invention sufficient to eliminate a painful condition will be administered. The actual dosage (concentration and volume) and the number of administrations per day will depend on the pharmacokinetic properties of the drug and the mode of drug administrations, for example, by topical doses to the eye.

In the present method, the compounds of the invention can be administered topically to non-ocular mucous membranes, such as for example oral, otic, nasal, respiratory, pharyngeal, tracheal, esophageal, urethral, or vaginal membranes. Formulations containing at least one compound of the invention useful for such membranes, may be for example solutions, sprays, suspensions, gels, creams or ointments. Compatible and pharmaceutically acceptable carriers, which may be used in this invention, comprise e.g. an aqueous solution, such as saline solutions, oil solutions or ointments. Formulations for ocular use may also contain compatible and pharmaceutically acceptable excipients, such as preservatives, surfactants, stabilizing agents, antibacterial agents, buffering agents and agents such as for example polymers to adjust viscosity, vasoconstrictors, antihistaminic agents or anti-inflammatory agents. Said formulations may be manufactured in different dosage units, suitable for ocular administration. Usually the concentration of active compound in a formulation for use on non-ocular mucous membranes is between 0.01 and 20% by weight. The quantity of the formulation containing the drug to be administered will be determined on an individual basis, and will be based on the pharmacological potency of the drug, the route of administration and at least in part in consideration of the individual's size, the severity of the symptoms to be treated and the results sought. In general, quantities of the local anesthetic compound of the invention sufficient to eliminate the unwanted condition will be administered. The actual dosage (concentration and volume) and the number of administrations per day will depend on the pharmacokinetic properties of the drug and the mode of drug administrations, for example, by topical doses to the mucous membranes of the mouth or throat.

Dosage units for rectal administration may be prepared in the form of ointments, gels, creams or suppositories, which contain the active substance in a mixture with a neutral fat base, or they may be prepared in the form of gelatin-rectal capsules that contain the active compound in a mixture with for example a vegetable oil or paraffin oil. Compatible and pharmaceutically acceptable carriers, which may be used in rectal formulations, also comprise aqueous solutions, gels, creams or ointments. Ointments, suppositories or creams containing at least one of the compounds of the invention are useful for the treatment of hemorrhoids and compounds of the invention having topical anesthetic effects in combination with compounds or excipients having vasoconstrictor effects or anti-inflammatory effects are particularly useful for the treatment of hemorrhoids and other types of rectal disorders. A compound of the inventions may be combined with a vasoconstrictor and/or an anti-inflammatory drug, such as for example a corticosteroid in a formulation for the treatment of hemorrhoids. Usually the concentration of active compound in a formulation for use on rectal membranes is between 0.02 and 20% by weight. The quantity of the formulation containing the drug to be administered will be determined on an individual basis, and will be based on the pharmacological potency of the drug, the route of administration and at least in part in consideration of the individual's size, the severity of the symptoms to be treated and the results sought. In general, quantities of the formulation containing the local anesthetic compound of the invention sufficient to eliminate the unwanted condition will be administered. The actual dosage (concentration and volume) and the number of administrations per day will depend on the pharmacokinetic properties of the drug and the mode of drug administrations, for example, by topical doses to the rectal membranes.

Dosage forms for dermal anesthesia may be prepared for example as solutions, gels, ointments, creams or sprays. The dermal composition may also contain emulsifiers, e.g. polyoxyethylene fatty acid esters, thickening agents, e.g. carboxypolymethylene, pH-adjusting agents, e.g. sodium hydroxide, preservatives, penetration promoting agents, e.g. hydroxypolyethoxydodecane, DMSO, DMAC, etc. The dermal composition may contain one or more active compounds and the compounds may be prepared as bases or salts to facilitate dermal penetration. Compositions may be delivered as a spray, which may be a preferred dosage form to patients suffering from severe dermal pain, such as patients suffering from shingles and other neuropathic pain conditions, for which the present invention will be of particular benefit. Composition may also be applied to the skin under occlusive dressing in a dermal delivery system ("patch" etc.) Usually the concentration of active compound in a formulation for dermal use is between 0.1 and 20% by weight of the composition. The quantity of the formulation containing the drug to be administered will be determined on an individual basis, and will be based on the pharmacological potency of the drug, possible dermal irritation or dermal toxicity of the drug, the route of administration and at least in part on the individual's size, the severity of the symptoms to be treated and the results sought. In general, quantities of the formulation containing the local anesthetic compound of the invention sufficient to eliminate an unwanted painful condition will be administered. The actual dosage (concentration and volume) and the number of administrations per day will depend on the pharmacokinetic properties of the drug and the mode of drug administrations, for example, by spray or by occlusive dermal formulation (patch).

The invention can be administered together with one or more other compound(s). For example, injectable solutions may contain a vasoconstrictor (e.g. epinephrine or vasopressin); a solution for infusion or regional anesthesia may contain glucose or dextrose, a gel for urogenital topical procedures may contain thickening agents (e.g. hydroxypropylmethylcellulose); a preparation for topical or dermal application may contain penetration promoting agents (e.g. hydroxypolyethoxydodecane, DMSO, DMAC); sprays for topical anesthesia of the mouth and oropharynx may contain saccharin and alcohol, ointments for accessible mucous membranes may contain a lubricant. The compounds of the invention can also be administered together with other membrane stabilizers (local anesthetics), for example to form eutectic mixtures. The compounds of the invention can also be administered together with other therapeutically active compounds, such as capsaicin, Substance-P inhibitors or antagonists, vaso-active compounds, anti-inflammatory agents, etc.

EXAMPLES

Example 1

Preparation of the Starting Material "SM-1", 2-(phenylamino)tetralin hydrochloride

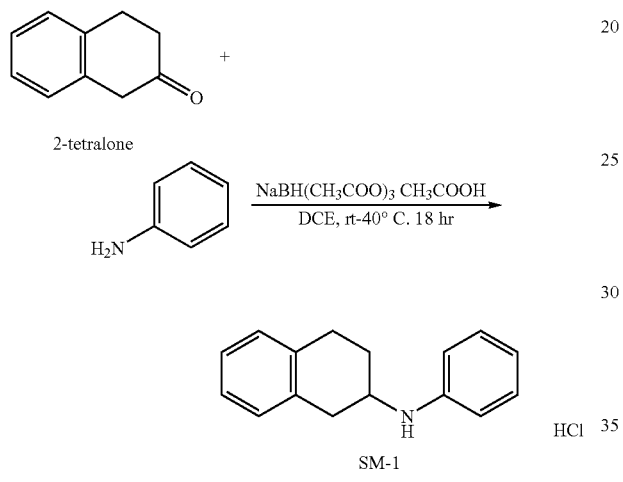

The method was similar to that of Abdel-Magid et al., J. Org. Chem. 61, 3849-3862, 1996. 2-Tetralone (22 g, 0.15 mol) and aniline (14 g, 0.15 mol) were mixed together at room temperature. An equivalent of glacial acetic acid (8.6 ml, 0.15 mol) was added in portions, and the temperature of the reaction mixture increased to 35° C. The reaction mixture was stirred for 15 minutes, and the temperature dropped to 22° C. The reaction mixture was diluted with 1,2-dichloroethane (DCE) 100 ml), and sodium triacetoxyborohydride (1.3 equiv) was added in portions at such a rate that the temperature was kept below 40° C. (Alternatively, other reducing agents such as sodium cyanoborohydride, borane-pyridine, Zn/acetic acid and metal-catalyzed hydrogenation (Pt, Pd, Ni) may be used in place of sodium triacetoxyborohydride.) The mixture was stirred at room temperature under $N_2$ until the reagents were consumed as determined by LC-MS analysis. The reaction was quenched by adding 1N aqueous NaOH (100 ml), and the product was extracted with diethyl ether (2×200 ml). The combined ether extracts were washed with 50% aqueous NaOH (1×100 ml) and the solvents evaporated to give the crude free base (27.4 g, 81% yield). The crude product was dissolved in diethyl ether (300 ml) and treated with 4.0M HCl in 1,4-dioxane (60 ml). The precipitate was filtered, washed with diethyl ether (2×30 ml), and dried under high vacuum to give 2-(phenylamino)tetralin hydrochloride, SM-1, (28 g, 88% yield) as a white solid. Melting point, $^1$H NMR and MS (mass spectrum) were consistent with the published data (Abdel-Magid et al., op cit.).

Example 2

Preparation of 2-{[2-(N-phenyl-N-(1,2,3,4-tetrahydronaphth-2-yl)amino]ethyl}piperidine (CLAC-34 hydrochloride)

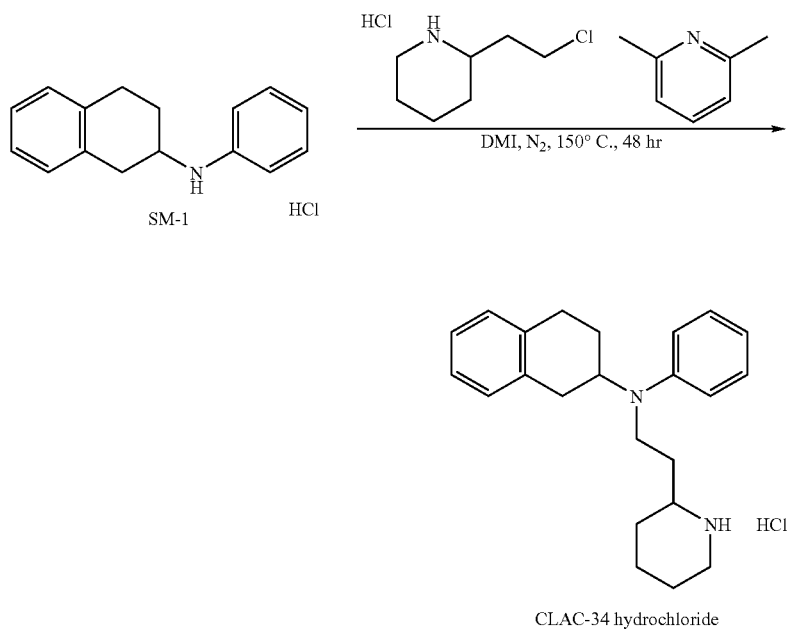

CLAC-34 hydrochloride 2-(Phenylamino)tetralin hydrochloride, SM-1, (10 g, 0.038 mol), 2-(2-chloroethyl)piperidine hydrochloride (8.1 g, 0.044 mol), 2,6-lutidine (16 ml, 0.0136 mol) and 1,3-dimethyl-2-imidazolidinone (DMI, 4 ml) were loaded in a 3 neck round bottom flask equipped with magnetic stirrer, thermometer, reflux condenser and nitrogen bubbler, and heated on an oil bath at 150° C. After 6 hours the reaction mixture solidified as a dark blue solid mass. After 48 hours, methanol (20 ml) was added slowly with stirring to the reaction mixture, and the mixture was kept under reflux for 30 min. After cooling to room temperature, the precipitate was filtered, washed with portions of methanol, and dried under vacuum to give CLAC-34 hydrochloride (3.7 g, 26% yield) as off-white, slightly bluish crystals. Purity >98% by HPLC. MS and $^1$H NMR were consistent with the structure. MS: (M+H)$^+$ 335 (calc 335.2). $^1$H NMR: consistent (FIG. 1).

Example 3

Preparation of 1-Butyl-2-{[2-(N-phenyl-N-(1,2,3,4-tetrahydronaphth-2-yl)amino]ethyl}piperidine (Bu-CLAC-34 hydrochloride)

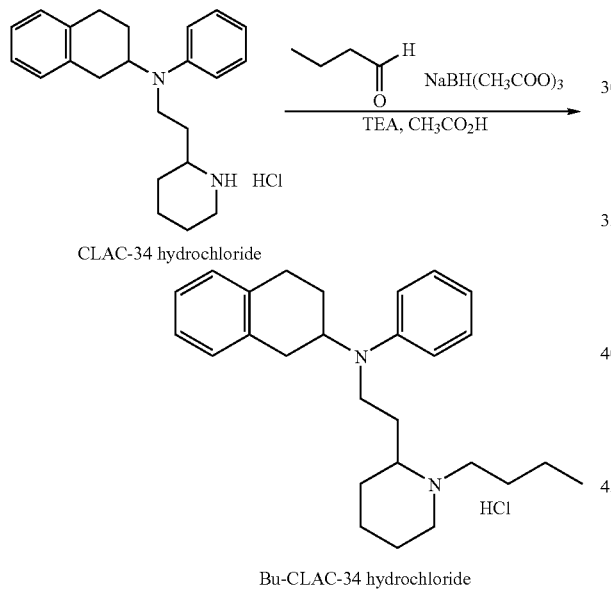

Figure 2:
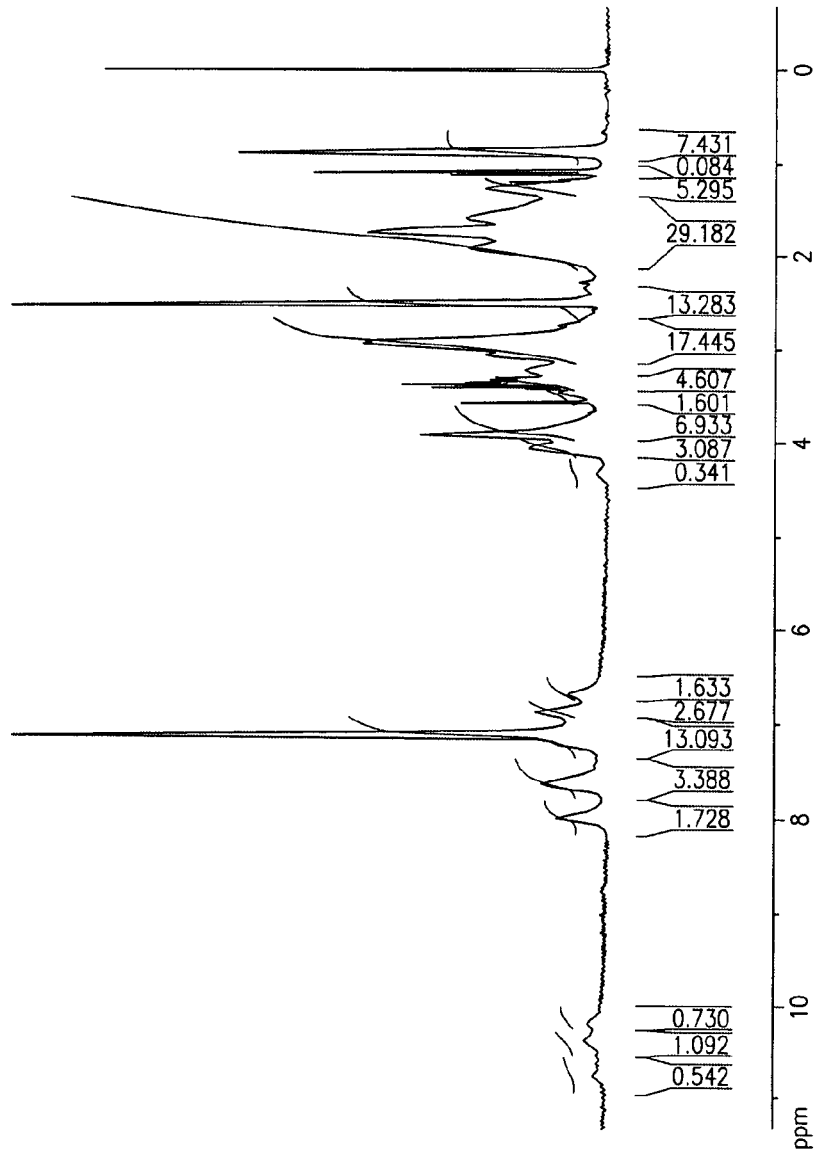
FIG. 2 is an NMR spectrum of the compound prepared in Example 3.

CLAC-34 hydrochloride (2 g, 5.4 mmol), butyraldehyde (0.39 g, 5.4 mmol) and triethylamine (TEA, 0.75 ml, 5.4 mmol) were mixed together at room temperature under an inert atmosphere. Glacial acetic acid (0.155 ml, 2.7 mmol) was added, and the temperature of the reaction mixture increased to 27° C. The reaction mixture was stirred for 15 minutes, and the temperature dropped back to 22° C. The reaction was diluted with 1,2-dichloroethane (DCE, 8 ml), and sodium triacetoxyborohydride (1.6 g, 1.4 equiv) was added in portions at such a rate that the temperature was kept below 40° C. The mixture was stirred at room temperature under N$_2$ for 12 hours. The reaction mixture was poured into 2M aqueous sodium bicarbonate (200 ml), and the product was extracted with ethyl acetate (2×150 ml). The organic solvent was removed under reduced pressure, and the oily residue was dissolved in 200 ml diethyl ether and washed with 50% aqueous sodium hydroxide (100 ml). The ether solution was treated with a solution of 4M hydrogen chloride in dioxane (4 ml) to give crude product. The crude product was dissolved in a solution of 1% triethylamine (TEA) in chloroform (100 ml), washed with water (2×50 ml), and the chloroform solution was loaded on a silica gel column. Elution with a gradient from 1% TEA in chloroform to 1% TEA in chloroform:methanol (10:1) gave the free base Bu-CLAC-34. The solvents were removed under vacuum, and the residue was dissolved in diethyl ether (100 ml). This solution was treated with a solution of 4M hydrogen chloride in dioxane (4 ml), and the precipitate was filtered, washed with diethyl ether (2×10 ml), and dried under high vacuum. Yield of Bu-CLAC-34 hydrochloride was 1.2 g (52%) as white crystals. Purity was >98% by HPLC. LCMS and $^1$H NMR were consistent with the structure. MS: (M+H)$^+$ 391 (calc 391.3). $^1$H NMR: consistent (FIG. 2).

Example 4

Preparation of N-(2-tetralyl)-N-phenyl-2-chloroacetamide

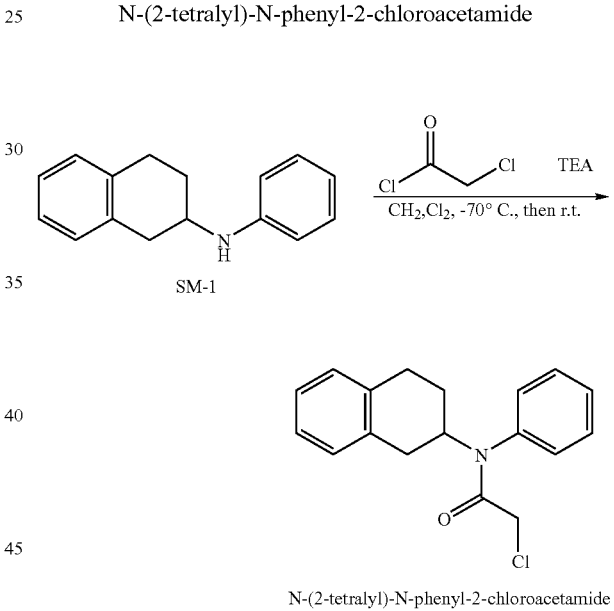

Figure 3:
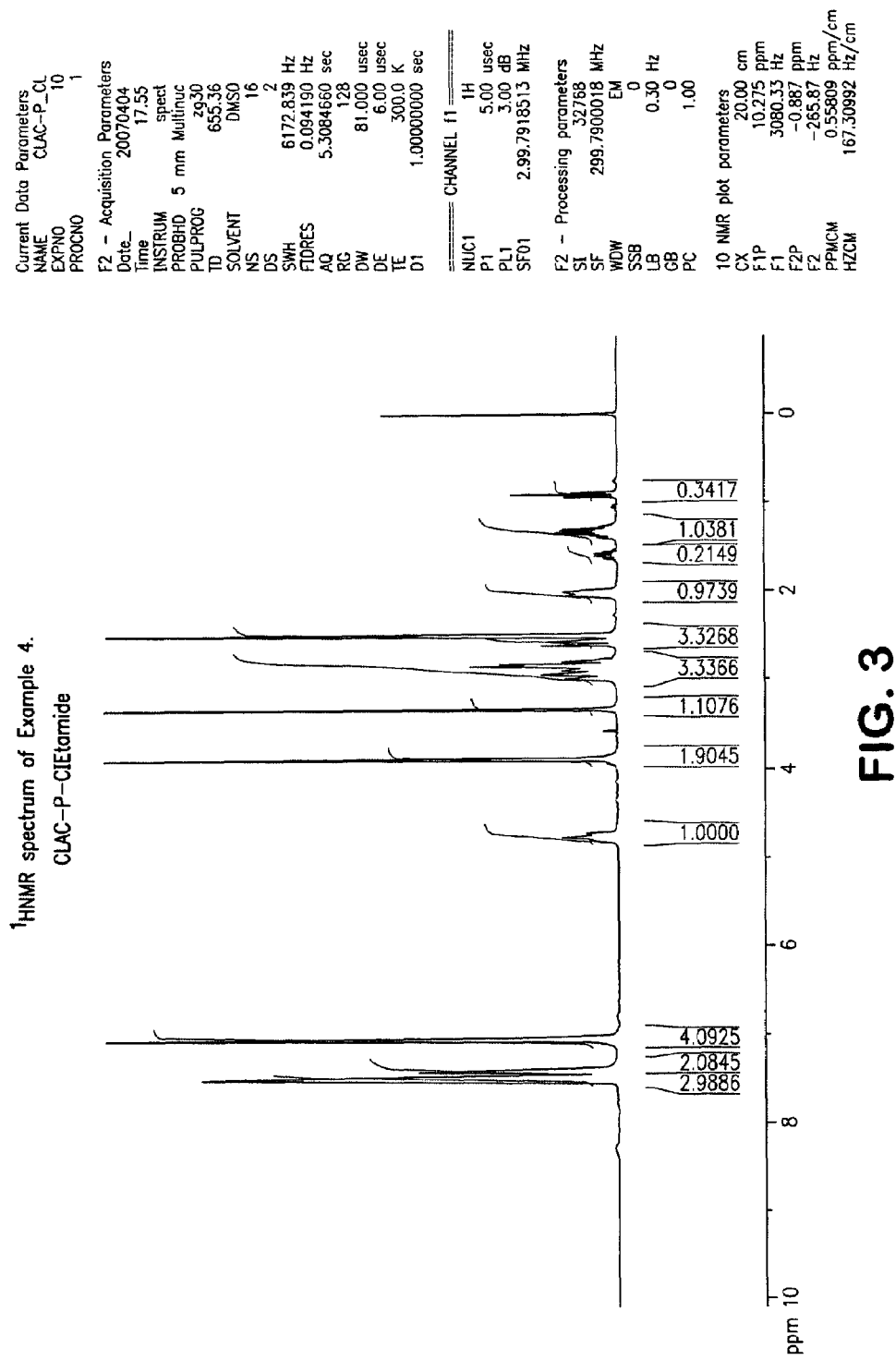
FIG. 3 is an NMR spectrum of the compound prepared in Example 4.

Chloroacetyl chloride (1.6 ml, 0.02 mol) was added to a cooled (dry ice/acetone) solution of 2-(phenylamino)tetralin free base (3 g, 0.01.3 mol) in 25 ml anhydrous dichloromethane containing triethylamine (TEA, 2.8 ml, 0.02 mol). The reaction mixture was stirred under nitrogen for 5 minutes. The cooling bath was removed, and the reaction was left to reach room temperature. The reaction mixture was diluted with dichloromethane (150 ml) and washed with water (3×100 ml), 5% aqueous citric acid (2×100 ml) and brine (1×100 ml), and the solvents were removed under vacuum. The oily residue was dissolved in 50 ml diethyl ether, and colorless needles rapidly crystallized. The product was filtered and dried to give 3.3 g (84%) of N-(2-tetralyl)-N-phenyl-2-chloroacetamide. Purity by HPLC was >99%. $^1$H NMR and MS were in agreement with the structure. MS: (M+H)$^+$ 300 (calc 300.1). $^1$H NMR: consistent (FIG. 3).

Example 5

Synthesis of N-(2-tetralyl)-N-phenyl-2-(N,N-dipropyl)acetamide

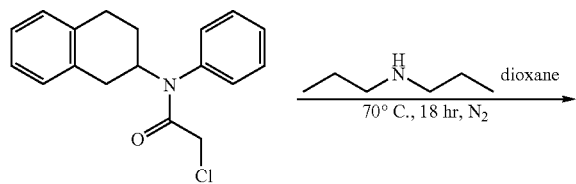

N-(2-tetralyl)-N-phenyl-2-chloroacetamide

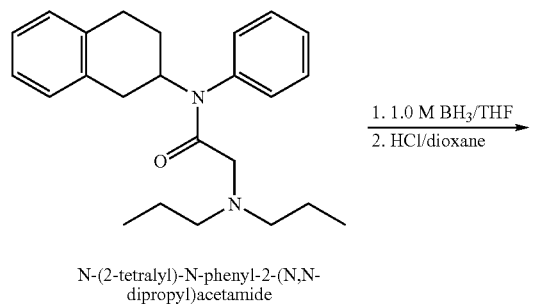

Figure 4:
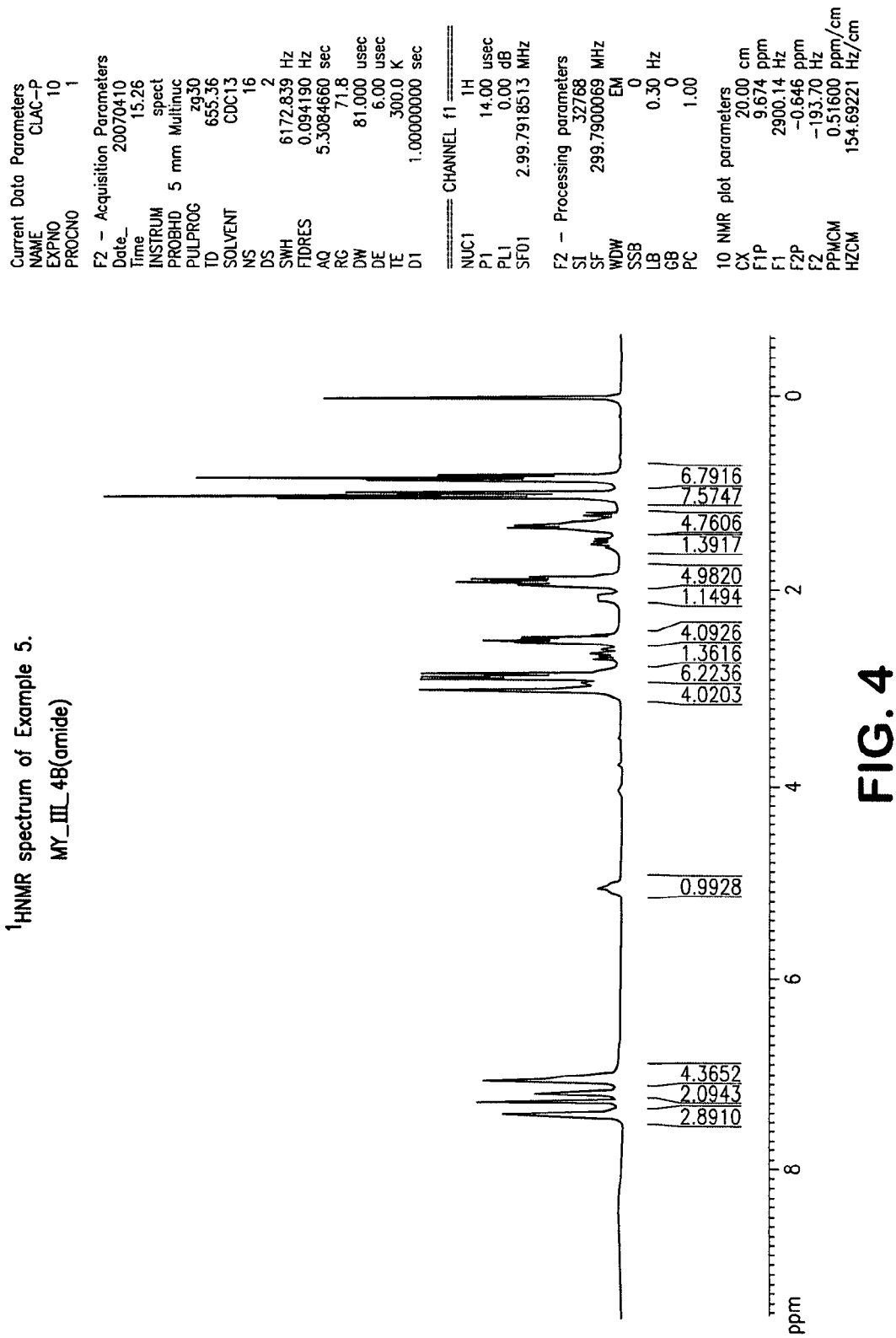
FIG. 4 is an NMR spectrum of the compound prepared in Example 5.

N-(2-tetralyl)-N-phenyl-2-(N,N-dipropyl)acetamide 1,4-Dioxane (10 ml) was added to a suspension of N-(2-tetralyl)-N-phenyl-2-chloroacetamide (3 g, 0.01 mol) in 50 ml n-dipropylamine, and the reaction mixture was heated at 70° C. for 18 hours under nitrogen. The solvents were removed under vacuum, and the residue was dissolved in 200 ml diethyl ether and washed with 10% aqueous sodium carbonate (2×100 ml). The diethyl ether layer was co-evaporated under reduced pressure with toluene (100 ml) to give 3.16 g (87%) of N-(2-tetralyl)-N-phenyl-2-(N,N-dipropyl)acetamide as a semisolid. Purity by HPLC was >98%. $^1$H NMR and MS were consistent with the structure. MS: (M+H)$^+$ 365.2 (calc 365.25). $^1$H NMR: consistent (FIG. 4).

Example 6

Synthesis of 1-[2-(N-phenyl-N-(1,2,3,4-tetrahydronaphth-2-yl)amino]-2-(N,N-dipropylamino)ethane (CLAC-PP dihydrochloride)

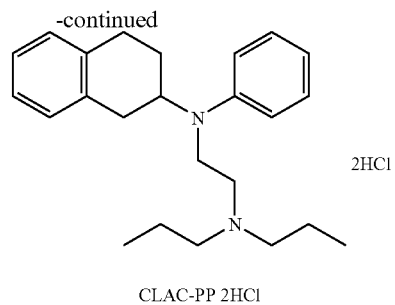

N-(2-tetralyl)-N-phenyl-2-(N,N-dipropyl)acetamide

CLAC-PP 2HCl

Figure 5:
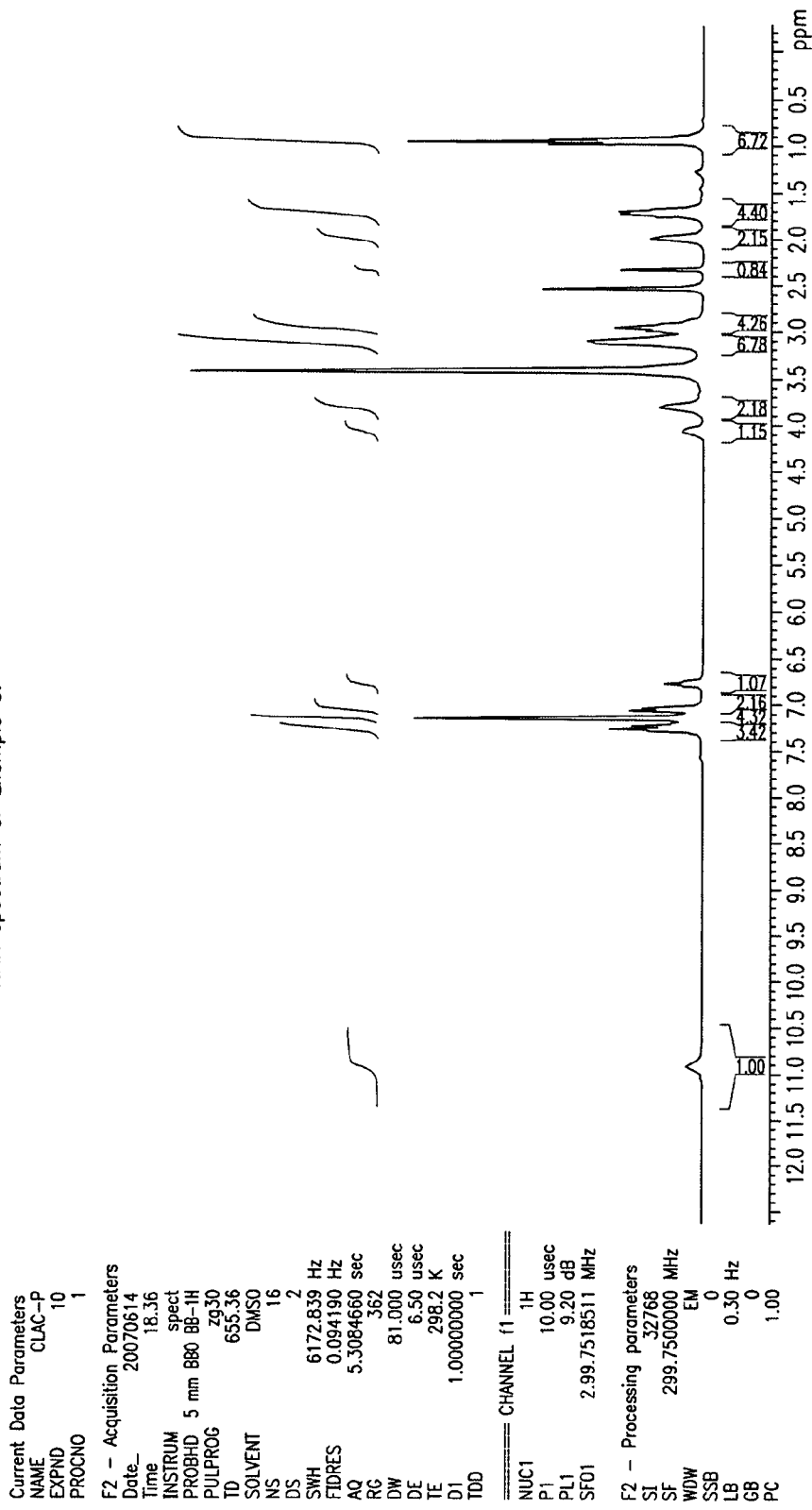
FIG. 5 is an NMR spectrum of the compound prepared in Example 6.

A solution of N-(2-tetralyl)-N-phenyl-2-(N,N-dipropyl)acetamide (3.16 g, 0.0067 mol) in 15 ml of anhydrous tetrahydrofuran was added to a cooled solution (ice bath) of 1.0 M borane in tetrahydrofuran (15 ml) over 10 minutes and under a nitrogen atmosphere. The colorless solution was heated at reflux for 4 hours. Fresh 1.0 M borane in tetrahydrofuran (7 ml) was added, and the reaction mixture was heated at reflux for 8 hours. The reaction mixture was allowed to cool to room temperature, and 5 ml of 6.0 M hydrochloric acid was added. The reaction was stirred at room temperature until the evolution of hydrogen ceased. The reaction mixture was kept at room temperature for 72 hours, and then heated to 60° C. for 1 hour. The reaction mixture was brought to room temperature, and tetrahydrofuran was removed under reduced pressure. The pH of the aqueous residue was adjusted to pH 10 with 1N aqueous sodium hydroxide, and extracted with diethyl ether (2×100 ml). The organic solvents were removed under reduced pressure, and the clear oil was co-evaporated with 100 ml of toluene. The residue was dissolved in diethyl ether (150 ml), the pH was adjusted to 3.5 with 4 M hydrogen chloride in dioxane, and the mixture was stirred at room temperature for 30 minutes. The colorless precipitate was filtered, washed with diethyl ether and dried under reduced pressure for 8 hours to afford 2.3 g (62.5%) of CLAC-PP dihydrochloride as a white hygroscopic solid. Purity by HPLC was 99%. $^1$H NMR and LCMS were in agreement with the structure. MS: (M+H)$^+$ 351.2 (calc 351.3). $^1$H NMR: consistent (FIG. 5). Other polar, volatile organic solvents such as tetrahydrofuran, methanol or ethanol can be used instead of dioxane.

Example 7

Synthesis of 1-[2-(N-phenyl-N-(1,2,3,4-tetrahydronaphth-2-yl)amino]-2-(N-propylamino)ethane (CLAC-HP dihydrochloride)

CLAC-HP is made by the same route as described for Example 6, but with replacement of dipropylamine by propylamine in Example 5.

Biological Testing

A. Affinity for Sodium Channels (Site 2).

Membrane homogenates of cerebral cortex (250 μg protein) were incubated for 60 min at 22° C. with 10 nM [$^3$H] batrachotoxinin in the absence or presence of the test compound in a buffer containing 50 mM Hepes/Tris (pH 7.4), 130 mM choline chloride, 5.4 mM KCl, 0.8 mM MgSO$_4$, 1 g/l glucose, 0.15 g/l scorpion venom and 0.1% BSA (Bovine Serum Albumin). Nonspecific binding was determined in the presence of 300 μM unlabelled veratridine. Following incubation, the samples were filtered rapidly under vacuum through glass fiber filters (GF/B, Packard) presoaked with 0.05% BSA and rinsed several times with an ice-cold buffer containing 50 mM Hepes/Tris (pH 7.4), 130 mM choline chloride and 0.8 mM $MgSO_4$ using a 96-sample cell harvester (Unifilter, Packard). The filters were dried then counted for radioactivity in a scintillation counter (Topcount, Packard) using a scintillation cocktail (Microscint 0, Packard).

The results are expressed as a percent inhibition of the control radioligand specific binding. The standard reference compound is lidocaine, which is tested in each experiment at several concentrations to obtain a competition curve from which its $IC_{50}$ is calculated.

|  | IC50 | Ki |
|---|---|---|
| CLAC-34•HCl (Example 2) | 2.0E–07 | 1.8E–07 |
| Bu-CLAC-34•HCl (Example 3) | 1.2E-0.7 | 1.1E–07 |
| CLAC-PP•HCl (Example 6) | 2.5E–07 | 2.2E–07 |
| Lidocaine.HCl *) | 2.3E–04 | 3.0E–0.4 |

*) Average from two experiments

It is concluded that the new compounds are approximately 900 to 1900 times more potent than lidocaine.

Tests according to this protocol of a compound of Formula 1, where $R_2$ is hydrogen (CLAC-HP; Example 7) are ongoing. Results indicate that secondary amines are also significantly more active than lidocaine.

B. Topical Anesthetic Activity.

Aliquots (0.25 ml) of test solutions are applied into the conjunctival sac of conscious rabbits (either sex; 2-4 kg) and the eye-lids are kept closed for approximately 20 sec. The corneal reflex is checked before application of the test solution and every 5 min thereafter. To test the corneal reflex, the cornea is touched six times with a stalked elastic bristle. The duration of anesthesia is calculated as the period from the time-point when the animal does not feel any of the six touches by the bristle to the time point when the animal again reacts to three of the six touches. To verify the reversibility of the topical anesthetic effect, the testing continues until the animal reacted to all six touches of the bristle for at least 15 minutes.

C. Dermal Anesthetic Activity.

Approximately 18-24 hours before each experiment, the skin on the back of male guinea pigs is shaved and depilated with a commercially available hair remover. The anesthetic action of each agent following dermal application is determined using a "pin-prick" method as described by Aberg (Acta Pharmacol Toxicol, 1972, 31: 273-286). Before and at various intervals after treatment, the areas of the skin are tested for the presence or absence of a skin twitch in response to six standardized dermal probings with a pointed metal "algesimeter" at a predetermined maximum load of 10 grams. The average number of probings not producing a skin twitch response is designated as the "anesthetic score". In this system six responses to six stimuli represents "no anesthetic activity" and no response to six stimuli represents a "maximal anesthetic activity". In experiments on dermal anesthetic activity, a single area of skin 1 inch square is marked off on the back of each animal. This area is covered by a 1 inch square, 16 layer thick gauze pad onto which was deposited 0.45 ml of a 10% solution of the test agent in water with DMSO. The gauze pad is covered with a 1.5 inch square sheet of Saran Wrap™ which is attached to the surrounding skin with tape. The entire area is then covered by wrapping an elastic bandage around the trunk of the animal. After a predetermined duration of treatment, the coverings are removed and the skin is assessed for the presence of anesthesia as described above. Dermal anesthesia is assessed at ten minute intervals to measure onset time and duration of dermal anesthetic activity; comparisons are made with reference compounds and vehicle. All test compounds are in the base form and dissolved in DMSO/water when tested for dermal anesthesia.

D. Local Anesthetic Activity (Infiltration Anesthesia).

Approximately 18-24 hours before each experiment, the skin on the back of male guinea pigs was shaved and depilated with a commercially available hair remover. The anesthetic action of each agent following intradermal injection was determined using a "pin-prick" method as described by Aberg (Acta Pharmacol Toxicol, 1972, 31: 273-286). Before and at various intervals after treatment, the area of the skin was tested for the presence or absence of a skin twitch in response to six standardized cutaneous probings with a pointed metal "algesimeter" at a predetermined maximum force of 20 grams. The average number of probings not producing a skin twitch response was designated as the "anesthetic score". In this system six responses to six stimuli represents "no anesthetic activity" and no response to six stimuli represents "maximal anesthetic activity". In experiments with intradermal injections of agents, the backs of the guinea pigs are divided into four sections using a marking pen, and 0.1 ml of 0.05%, 0.1% and 0.25% solutions of the test compounds, 0.1 ml of the vehicle and solutions of a reference compounds were injected, one injection into each of the four defined areas. Duration of anesthesia is defined as the time from drug injection until 50% of the maximal anesthetic effect remains (indicated as 18/36 in the following table). As an example, the duration of lidocaine 1.0% was between 30 min and 60 min. The duration of dermal anesthesia by the new compounds were >>120 min. The in vitro test results are confirmed by in vivo test results.

Dermal Anesthesia after Intradermal Drug Injections:

| Test Article and Conc. | Time Period (minutes) | | | | |
|---|---|---|---|---|---|
|  | 15 | 30 | 60 | 90 | 120 |
| CLAC 34/0.05% | 35/36* | 36/36** | 6/36 | 36/36 | 36/36 |
| CLAC 34/0.10% | 36/36 | 36/36 | 36/36 | 36/36 | 36/36 |
| CLAC 34/0.25% | NT | NT | NT | NT | NT |
| Bu-CLAC 34/0.05% | 36/36 | 36/36 | 36/36 | 36/36 | 36/36 |
| Bu-CLAC 34/0.10% | 36/36 | 36/36 | 36/36 | 36/36 | 36/36 |
| Bu-CLAC 34/0.25% | NT | NT | NT | NT | NT |
| CLAC PP/0.05% | 36/36 | 36/36 | 36/36 | 36/36 | 36/36 |
| CLAC PP/0.10% | 36/36 | 36/36 | 36/36 | 36/36 | 36/36 |
| CLAC PP/0.25% | NT | NT | NT | NT | NT |
| Lidocaine/0.25% | 31/36 | 21/36 | 6/36 | 4/36 | 1/36 |
| Lidocaine/0.50% | 24/36 | 18/36 | 11/36 | 10/36 | 9/36 |
| Lidocaine/1.00% | 32/36 | 28/36 | 9/36 | 8/36 | 6/36 |

*35/36 indicates that 35 of 36 pinpricks were judged as non-responding pinpricks.
**36/36 indicates full anesthesia.
NT = Not Tested.

E. Acute Intravenous Toxicity in Mice.

Mice (males) of the NMRI strain, weighing 20 to 22 g are used after a stabilization period of at least ten days at the testing facility and at least one hour in the laboratory. Food but not water has been withheld from all animals for 16 hours before the test. The animals are given free access to food starting two hours after the drug administration, that usually takes place around 9.00 AM. All animals are observed daily for 7 days post dosing.

EQUIVALENTS

Those skilled in the art will recognize, or be able to ascertain, using no more than routine experimentation, many equivalents to the specific embodiments of the invention described herein. The compounds of the present invention may be used also for other indications where inhibition of sodium channels are beneficial, such as for example to prevent or treat smooth muscle spasms, including spasms of facial smooth muscles, cardiac arrhythmias, convulsions, tinnitus and hiccup. The use of a polymorph may have beneficial physico-chemical properties which, for example may improve solubility or stability and may also improve biological effects such as for example trans-membrane transport of the molecule. All polymorphs are encompassed in the scope of the present claims. The use of a single isomer may have the advantage that side effects residing in the other isomer can be avoided. Thus nervous system side effects, effects on respiration and cardiovascular side effects, such as for example negative inotropic effects, negative chronotropic effects and negative dromotropic effects may be completely or partially avoided by using a single isomer. All isomers are encompassed in the scope of the present claims. Formulations containing at least one compound of the present invention may also be injected or instilled into various cavities of the body, including the urinary bladder. All administration forms are encompassed in the scopes of the current claims. All equivalents are intended to be encompassed in the scope of the following claims.

We claim:
1. A compound having the formula 1:

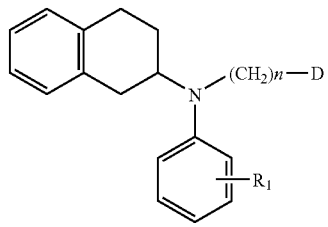

formula I or an optically active isomer thereof, wherein $R_1$ is, independently, one or more H, halo or lower (C1-C6) alkyl group(s), substituted at the 2, 3 and or 4 positions of the phenyl ring and wherein n is equal to 1, 2, 3 or 4 and wherein D represents a group of the formula 2:

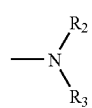

(Formula 2)

in which $R_3$ represents hydrogen, and $R_2$ forms, together with the adjacent carbon atom of the $(CH_2)_n$ group a nitrogenous heterocyclic ring, selected from the group consisting of un-substituted piperidino, pyrrolidino, pyridino, morpholino, quinuclidino, decahydroquinolino, decahydroisoquinolino and piperazino rings and substituted piperidino, pyrrolidino, morpholino, decahydroquinolino, decahydroisoquinolino and piperazino rings, and when substituted, the nitrogen substituent of said rings is selected from the group consisting of methyl, ethyl, propyl, butyl, hydroxyethyl, hydroxypropyl or hydroxybutyl and where appropriate, said nitrogenous heterocyclic ring is attached at 2-, 3- or 4-position, or a pharmaceutically acceptable salt thereof.

2. A pharmaceutical composition for induction of local anesthesia, comprising a pharmaceutically acceptable carrier and, as an active agent, a therapeutically effective amount of at least one compound of the general formula 1:

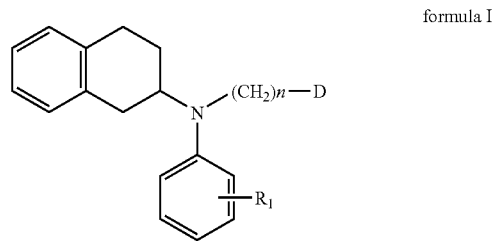

formula I or an optically active isomer thereof, wherein $R_1$ is, independently, one or more H, halo or lower (C1-C6) alkyl group(s), substituted at the 2, 3 and or 4 positions of the phenyl ring and wherein n is equal to 1, 2, 3 or 4 and wherein D represents a group of the formula 2:

(Formula 2)

in which $R_2$ represents hydrogen, a lower alkyl or hydroxyalkyl radical containing 1 to 4 carbon atoms, $R_3$ represents a lower alkyl or hydroxyalkyl radical containing 1 to 4 carbon atoms or a lower alkenyl or alkynyl radical containing 2, 3 or 4 carbon atoms, whereby $R_2$ and $R_3$ may be identical or different and $R_2$ may also form together with the adjacent carbon atom of the $(CH_2)_n$ group a nitrogenous heterocyclic ring, attached in any position and selected from the group consisting of un-substituted piperidino, pyrrolidino, pyridino, morpholino, quinuclidino, decahydroquinolino, decahydroisoquinolino and piperazino rings and substituted piperidino, pyrrolidino, morpholino, decahydroquinolino, decahydroisoquinolino and piperazino rings, and wherein when substituted, the nitrogen substituent of said rings is selected from the group consisting of methyl, ethyl, propyl, butyl, hydroxyethyl, hydroxypropyl or hydroxybutyl and where appropriate said nitrogenous heterocyclic ring is attached at 1-, 2-, 3- or 4-position, or a pharmaceutically acceptable salt thereof.

3. The pharmaceutical composition of claim 2, wherein said local anesthesia is selected from the group consisting of dermal anesthesia, topical anesthesia, infiltration anesthesia and nerve blocks.

4. The pharmaceutical composition according to claim 2, wherein said local anesthesia is dermal anesthesia and wherein said compound comprises 0.1 to 20% by weight of the composition.

5. The pharmaceutical composition according to claim 2, wherein said local anesthesia is topical anesthesia and wherein the compound comprises 0.05 to 20% by weight of the composition.

6. The pharmaceutical composition according to claim 2, wherein said local anesthesia is rectal anesthesia and wherein the compound comprises 0.02 to 20% by weight of the composition.

7. The pharmaceutical composition according to claim 2, wherein said local anesthesia is ocular anesthesia and wherein the compound comprises 0.05 to 2.5% by weight of the composition.

8. The pharmaceutical composition according to claim 4, wherein said local anesthesia is infiltration anesthesia and wherein said compound comprises 0.01 to 5% by weight of the composition.

9. The pharmaceutical composition according to claim 4, wherein said local anesthesia is nerve blocks and wherein said compound comprises 0.01 to 5% by weight of the composition.

10. The pharmaceutical composition of claim 2, wherein said composition is for the treatment of neuropathic pain.

11. The pharmaceutical composition of claim 2, wherein said Compound is 2-{[2-(N-phenyl-N-(1,2,3,4-tetrahydronaphth-2-yl)amino]ethyl}piperidine or a pharmaceutically acceptable salt thereof.

12. The pharmaceutical composition of claim 2, wherein said compound is 1-Butyl-2-{[2-(N-phenyl-N-(1,2,3,4-tetrahydronaphth-2-yl)amino]ethyl}piperidine or a pharmaceutically acceptable salt thereof.

13. The compound of claim 1, wherein said compound is 2-{[2-(N-phenyl-N-(1,2,3, 4 tetrahydronaphth-2-yl)amino]ethyl}piperidine or a pharmaceutically acceptable salt thereof.

14. The compound of claim 1, wherein said compound is 1-Butyl-2-{[2-(N-phenyl-N-(1,2,3,4-tetrahydronaphth-2-yl)amino]ethyl}piperidine or a pharmaceutically acceptable salt thereof.

* * * * *